United States Patent [19]
Serota

[11] Patent Number: 4,865,978
[45] Date of Patent: Sep. 12, 1989

[54] LIPOLYTIC SPLITTING OF FATS AND OILS

[75] Inventor: Samuel Serota, Philadelphia, Pa.

[73] Assignee: The United States of America as represented by the Secretary of Agriculture, Washington, D.C.

[21] Appl. No.: 882,103

[22] Filed: Jul. 3, 1986

[51] Int. Cl.$^4$ ............................................. C12P 7/64
[52] U.S. Cl. .................................. 435/134; 435/159; 435/198; 435/921
[58] Field of Search ............... 435/134, 159, 198, 271, 435/287, 316, 921; 422/129.1

[56] References Cited

U.S. PATENT DOCUMENTS 3,012,977  12/1961  Wilson et al. ................... 422/133

FOREIGN PATENT DOCUMENTS 57-57799  4/1982  Japan ................................ 435/134
59-20399  2/1984  Japan ................................ 422/129.1
60-237997 10/1985  Japan ................................ 435/134

OTHER PUBLICATIONS

JAOCS, vol. 61, No. 2, (Feb. 1984), pp. 191–195.
Levenspeil, Octave, *Chemical Reaction Engineering*, Wiley & Sons, Inc., 1972, pp. 133–143.
JAOCS, vol. 61, No. 6 (Jun. 1984), pp. 1067–1071.
JAOCS, vol. 62, No. 7 (Jul. 1985), pp. 1152–1154.
J. Ferment. Technol., V. 60, No. 6, pp. 517–523 (1982).
JAOCS, V. 62, No. 2, pp. 335–340, (Feb. 1985).
Chem. Abstracts, V. 76, cit. no. 125614d.
Chem. Abstracts, V. 99, cit. no. 160280p.
Chem. Abstracts, V. 88, cit. no. 166377v.
Chem. Abstracts, V. 86, cit. no. 117283m.
Chem. Abstracts, V. 84, cit. no. 118171u.
Chem. Abstracts, V. 85, cit. no. 145160s.
Chem. Abstracts, V. 97, cit. no. 22102q.
Chem. Abstracts, V. 83, cit. no. 175165y.
Chem. Abstracts, V. 79, cit. no. 51843r.
Chem. Abstracts, V. 78, cit. no. 94577d.

*Primary Examiner*—Barry S. Richman
*Assistant Examiner*—Timothy M. McMahon
*Attorney, Agent, or Firm*—M. Howard Silverstein

[57] ABSTRACT

Triglycerides in fats and oils are lipase-hydrolyzed to fatty acids and glycerol, in the absence of surfactants, wherein much less lipase is employed than previously used, and yet essentially all the triglycerides are hydrolyzed. A special mixer is used having impeller blades, baffles to prevent mass swirling, and a spiral heating/cooling coil.

30 Claims, 1 Drawing Sheet

LIPOLYTIC SPLITTING OF FATS AND OILS

PRIOR ART

It is known in the prior art that triglycerides in animal, plant and marine fats and oils are hydrolyzable into valuable fatty acids and glycerol. Further it is known that catalytic hydrolysis (splitting), e. g., lipase enzyme as the catalyst, provides several advantages including reaction conditions at atmospheric pressure and comparatively low temperatures. The lipase catalytically hydrolyzes the triglycerides at the oil-water interface. In order to increase this interface, in some cases emulsifiers have been employed.

To date catalytic hydrolysis with lipase has been reported to hydrolyze 95% of beef tallow. See JAOCS, vol. 62, no. 2, February, 1985, pp 335–340; and Nippon Kagaku Kaishi vol. 9, 1983, pp 1358-62. Since tallow ordinarily contains slight amounts of nonsaponifiables, a 95% conversion means that about 4% or more of the triglycerides remain unhydrolyzed, and are present as impurities in the hydrolysis reaction product. Such a product, without further purification, is suitable only for soaps. *Candida rugosa* lipase has been used to hydrolyze tallow triglycerides at 30°-35° C. wherein the tallow remains in the solid phase during hydrolysis. Higher operating temperatures with *C. rugosa* lipase ordinarily have been avoided because this particular lipase is believed to be less active or inactive at higher temperatures.

Palm oil triglycerides previously have been reported as being 96–98% converted by lipase. See above-cited JAOCS article. A 98% conversion means that about 1.8% of the triglycerides in ordinary palm oil remain unhydrolyzed, for the reasons explained above with regard to tallow, and therefore are present in the hydrolysis reaction product as impurities. Such a palm oil conversion product has some utility beyond soaps, e. g., as shampoo and a feedstock for production of some alcohols, esters and surfactants. However, the individual fatty acids in palm oil hydrolysis product still contain some unhydrolyzed triglycerides, and therefore the use thereof is limited without further purification.

SUMMARY

I now have been able to form a lipase hydrolysis product containing essentially no triglycerides therein, i. e., no more than 0.3% of the triglycerides remain unhydrolyzed, while employing far less lipase per gram of fat or oil than previously used.

In my invention the triglycerides, water and lipase are mixed together in such a manner as to form a pseudoemulsion in the absence of emulsifier, and the pseudoemulsion is maintained until less than 0.3% of the triglycerides remain unhydrolyzed. As used in the specification and claims, the term "pseudoemulsion" means that the oil phase is divided into emulsion-size particles suspended in the aqueous phase during mixing, but that these particles rapidly coalesce upon termination of the mixing action. The step of maintaining the pseudoemulsion throughout the requisite time period is accomplished by a combination of two steps: (a) the mixture is continuously stirred at a speed sufficient to create a pseudoemulsion, and (b) the pseudoemulsion is continuously impelled against baffles in the mixing zone affording turbulence to prevent mass swirling in the mixing zone.

Further, I have discovered that *C. rugosa* lipase can be used at about 40° C. to hydrolyze tallow, without a reduction in conversion. In fact, at about 40° C., even tallow with a titre (melting point) of 43° C. becomes fluid-like during mixing, but not necessarily melted, which enhances interface contact between the aqueous and oil phases.

The reaction products of the present invention, i. e., oily component (fatty acids), and aqueous component (glycerol) known as sweet water, readily separate upon standing into distinct layers (without centrifuging) with an easily removable film of denatured lipase therebetween.

I have discovered that my hydrolysis reaction can be achieved in an impeller blade mixer of the type previously employed in the fermentation art to produce microorganisms, modified to operate at much higher rpm, thereby to continuously form a pseudoemulsion. The mixer includes radially-positioned baffles against which the pseudoemulsion is continuously impelled, producing turbulence thereby preventing mass swirling.

Still further, during my hydrolysis reaction, polyethylene, often present in minute quantities as an impurity in rendered fats, readily separates out as an easily removable film or fuzz-like deposit on the blades of the mixer, and as an easily removable fuzz-like deposit on the denatured lipase film which forms between the aqueous and oil layers after the mixing action is terminated.

Therefore, it is an object of the present invention to provide lipase hydrolysis of triglycerides while employing minimal amounts of lipase.

Another object is to hydrolyze (split) all the triglycerides to fatty acids and glycerol.

A further object is to convert all the triglycerides while using far less of the relatively expensive lipase than previously used for attaining lower conversions.

A still further object is to hydrolyze tallow with *C. rugosa* lipase at a temperature higher than previously employed, without loss of the degree of conversion.

Still another object is to provide a reaction product containing an oily component and an aqueous component which readily separates into distinct layers.

Other objects and advantages will be obvious from the following more detailed description in conjunction with the drawings in which FIG. 1 is a cut-out, three-dimensional view, and FIG. 2 is a cross-sectional view.

DETAILED DESCRIPTION

Figure 1:
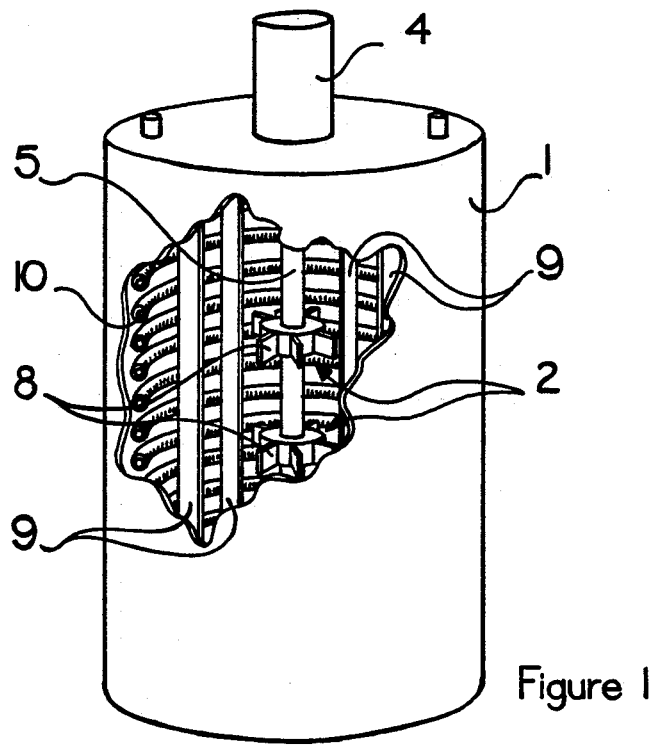

In the practice of the present invention, the feedstock ingredients, i. e., the aqueous phase, the oil or fat, and the lipase, are the same as those in the prior art. Any lipase may be employed which is known to catalytically hydrolyze all the glyceride components of the triglyceride feedstock, i. e., known to randomly (completely) hydrolyze the triglycerides. Presently, these lipases belong to a class designated as EC 3.1.1.3.

The ratio of oil or fat to aqueous phase is the same as that employed in the prior art, e. g., about 1:0.9 to 1:1.5, preferably about 1:1.2, by weight.

Triglyceride feedstocks include greases, fish oil, palm oil, soybean oil, coconut oil, tallow and so forth. Yellow, odorous residual greases formed after deep oil-frying of foods such as french fries, fish and chicken readily can be hydrolyzed by the present invention to clear, odorless fatty acids and glycerol.

Some triglyceride feedstocks such as tallow, rapeseed or yellow grease sometimes contain lipase-inhibiting componets. Accordingly, these feedstocks preferably are tested for the presence of such constituents. If the inhibitor is present, the triglyceride feedstock is treated with special bleaching clays (acid activated bentonite or montmorillonite) to remove the inhibitor, as is known in the prior art. For example, the oil or fat is warmed; the clay is stirred therein; a vacuum is applied to remove moisture and air from the clay; the mixture is stirred while being cooled, and then filtered to remove clay. The filtrate (oil phase) then may be treated by the lipase hydrolysis of the present invention. As used herein, the term "bleached" means that the feedstock has been pre-treated to remove lipase-inhibiting constituents.

The aqueous phase of the feedstock ordinarily is buffered water although excellent results are obtainable with unbuffered solutions. The pH range may be about 4.5-7.0, preferably about 5.5-6.0. In the case of buffer pairs such as $NaH_2PO_4$ and $Na_2HPO_4$, molarities are about 0.05 to 0.5, preferably about 0.1 to 0.2. Lipase may be dissolved in the water phase of the feedstock, or dissolved in a small amount of water and then added to the water phase already in the reactor.

No emulsifiers or surfactants are present in the hydrolysis reaction of the present invention, and the lipase is employed in far less amounts per gram of oil or fat than previously employed. Since lipase hydrolysis activity varies depending upon the type of lipase or purity thereof, the amount of lipase to be employed may be determined by measuring the activity of the candidate lipase in accordance with JAOCS, volume 62, p1152, 1985, "A New Method for the Assay of Lipase Activity". On the basis of such activity, the lipase generally is employed in the present invention in an amount which produces about 33-80 units of activity per gram of oil or fat, wherein 1 unit equals the amount which generates 1 micromole of free fatty acid in bleached olive oil per minute in accordance with the above cited test. More preferably, the lipase is present in an amount which produces about 33-50 units of activity per gram of oil or fat. Still more preferably, the lipase is present in an amount which produces about 33 units of activity per gram of oil or fat, affording the largest amount of desired products per unit cost of lipase.

Ordinarily, the hydrolysis reaction is carried out in air. However, in the case of highly unsaturated triglycerides such as linseed oil or marine oils, the reaction may be carried out in an inert environment such as nitrogen.

Operating temperatures will vary in accordance with the type of lipase, usually from about 20° C. to 45° C., preferably about 30° C. to 45° C. Lipase is known to rapidly degrade above specified temperatures for each type, and thus such temperatures are to be avoided. For example, *C. rugosa* lipase degrades considerably at 42° C., whereby this temperature should be avoided when using such a lipase. However even though *C. rugosa* lipase is known to be less active above 37° C., an operating temperature of about 40° C. (39.5 to 41° C.) preferably is employed in the practice of the present invention when hydrolyzing tallow because it becomes fluid-like in the mixer, not melted, which apparently more than compensates for any loss of activity in the lipase.

Reaction times will vary depending upon the fat or oil being hydrolyzed. For example, tallow may require about 72 hours, while many vegetable oils are hydrolyzed in about 24 hours.

As previously noted, the present invention can convert 100% of the triglycerides to fatty acids and glycerol. Generally, no more than 0.3% of the triglycerides remained unhydrolyzed. In several tests to date, no triglycerides have been detected in the hydrolysis product, although a re-test of one of these latter tests showed that 0.2% of the triglycerides remained unhydrolyzed. Such a degree of purity in a lipase hydrolysis reaction product was unheard of in this art, prior to the present invention.

After the hydrolysis reaction, the oil component (fatty acids) and the aqueous component (glycerol) easily are separated into two layers by standing, particularly because of the absence of emulsifiers. In the case of *C. rugosa* lipase hydrolysis of tallow, the product separates into the two layers in about 20 minutes at the reaction temperature (about 40° C.), and will separate in about 5 minutes if the temperature is raised about 5°-10° C.

Spent lipase catalyst forms as a thin film between the layers in the separation zone. It is easily removed by allowing the aqueous (lower) phase to pass out of the separation chamber, and thereafter capturing the lipase film on a cheesecloth or screen as the last of the water phase and a very slight amount of the oil phase are passed through the cheesecloth. The proteinaceous content of the lipase makes it suitable as animal feed.

Very valuable glycerol is recovered from the aqueous phase (sweet water) by multi-effect evaporation which removes the water.

Referring now to the mixer of the present invention, reference numeral 1 designates the hydrolysis reactor. Impellers 2, which provide the mixing, are driven by a motor 4 through shaft 5. Stirring speeds of about 200-1500 rpm are employed preferably about 400-1000 rpm.

Figure 2:
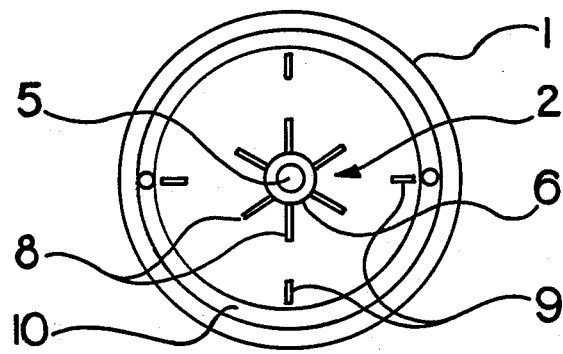

As can be seen in FIG. 2, each impeller consists of a ring 6 secured in a conventional manner to shaft 5, and a plurality of blades 8, preferably 4-6 blades, secured to the ring.

A plurality of radially-positioned baffles 9, preferably four baffles, are connected to the upper and lower walls of the reactor 1 in the zone between the outer edge of the blades and the inner wall of the reactor. These baffles prevent mass swirling of the mixture, and thus increase turbulence, thereby providing, in combination with rapidly moving impellers 2, a very large oil-water interface (pseudoemulsion) throughout essentially the entire mixture in the mixing zone, to maximize the rate and degree of hydrolysis.

While the hydrolysis essentially is non-exothermic, heat can be generated at the high speeds of rotation at the bearings and/or by the agitation of the impeller blades rotating through the pseudoemulsion. It is important to remove this heat and to control the hydrolysis reaction temperature, for the reasons explained above. For this purpose, a spiral water-containing heating-/cooling coil is positioned in the reactor chamber between the reactor's inner wall and the baffles 9. The coil may be combined with temperature sensing means including bimetallics, thermocouples or thermisters.

The ratio of feedstock volume to impeller blade area, in ml per sq. cm., should be no more than about 35:1, preferably no more than about 25:1.

The system can be operated on a continuous basis (cascade) by pumping reaction product to a second or downstream reactor after about 30% hydrolysis, and simultaneously replenishing the first reactor with fresh feed. A series of three or four reactors operating in this manner, in which each reactor is replenished with feed from the reactor immediately upstream as its material is transferred to a reactor immediately downstream, will provide the same degree of hydrolysis in less time than a single reactor.

The materials of construction for the reactor may be, for example, wood, stainless steel, ceramic coated steel, plastic or fiber glass.

An additional advantage of the present invention pertains to the removal of polyethylene impurities from the triglycerides. In rendering plants, polyethylene-wrapped meats are rendered in their original packaging which results in particles of polyethylene becoming dispersed in the hot tallow during the rendering process. Typically, such tallows contain about 200 ppm of polyethylene. Subsequently, when conventional high temperature hydrolysis is employed to split these fats, the polyethylene plates out, as an enamel-like coating, on heat exchange surfaces, and requires considerable effort, with jack-hammer-like tools, to remove the coating. In the present invention, if polyethylene is present, it separates out as a film or fuzz-like deposit on the mixer blades which is easily removed with a hot water wash, and it additionally separates out, after hydrolysis, as a fuzz-like deposit on the thin film of spent lipase which forms between the aqueous and oil layers in the separation zone. The oil and aqueous layers are polyethylene-free.

The following is a description of a laboratory test of the present invention which resulted in a hydrolysis product containing no detectable unreacted triglycerides.

The test was conducted in a Brunswick Scientific mixer previously used in the fermentation art to grow microorganisms, except that the mixer's bearing had been altered to accomodate much higher revolution speeds, and a spiral cooling coil as described in FIG. 1 was added thereto. The mixers dimensions were approximately 11 cm in diameter by 30 cm in height.

The unit contained two 316 stainless steel 6-blade turbine impellers powered by a continuous-duty high speed drive. each blade was about 1.2 cm high, and 1.8 cm in length. Four flat vertical baffles, as described in FIG. 1, were employed to prevent mass swirling. The feedstock comprised 375 g tallow and 435 g of aqueous solution. The aqueous solution consisted of 623 mg of *C. rugosa* lipase in distilled water. Lipase activity was 33 units per gram of tallow. Hydrolysis temperature was 40° C. Stirring speed was about 900 rpm. The reaction was carried out for 72 hours.

I claim:

1. A method of hydrolyzing triglycerides in fats and oils to fatty acids and glycerol comprising
   forming a pseudoemulsion of said triglycerides in water and lipase, said lipase being present in an amount of about 33–80 units of activity per gram of said triglycerides, and maintaining said pseudoemulsion until less than 0.3% of said triglycerides remain unhydrolyzed.

2. The method of claim 1 wherein said pseudoemulsion is formed in the absence of the addition of emulsifier.

3. The method of claim 1 wherein said triglycerides include minute quantitities of polyethylene as an impurity, further comprising forming said polyethylene as an easily removable fuzz-like deposit during said hydrolysis.

4. The method of claim 3 wherein said pseudoemulsion is formed in the absence of the addition of emulsifier.

5. The method of claim 1 wherein said lipase is present in an amount of about 33–50 units of activity per gram of said triglycerides.

6. The method of claim 5 wherein said pseudoemulsion is formed in the absence of the addition of emulsifier.

7. The method of claim 5 wherein said triglycerides are in tallow, wherein said lipase is *C. rugosa* lipase, and wherein said steps of forming and maintaining said pseudoemulsion are carried out at about 40° C. and below said tallow's melting point.

8. The method of claim 1 wherein the step of maintaining said pseudoemulsion comprises (a) continuously stirring said triglycerides, water and lipase in a mixing zone at a speed sufficient to form a pseudoemulsion, and (b) continuously impelling said pseudoemulsion against baffles in said mixing zone to prevent mass swirling in said mixing zone.

9. The method of claim 8 wherein said pseudoemulsion is formed in the absence of the addition of emulsifier.

10. The method of claim 8 wherein said lipase is present in an amount of about 33 units of activity per gram of said triglycerides.

11. The method of claim 10 wherein said triglycerides are in tallow, wherein said lipase is *C. rugosa* lipase, and wherein said steps of forming and maintaining said pseudoemulsion are carried out at about 40° C. and below said tallow's melting point.

12. The method of claim 8 wherein said lipase is present in an amount of about 33–50 units of activity per gram of said triglycerides.

13. The method of claim 12 wherein said triglycerides are in tallow wherein said lipase is *C. rugosa* lipase, and wherein said steps of forming and maintaining said pseudoemulsion are carried out at about 40° C. and below said tallow's melting point.

14. The method of claim 13 wherein said pseudoemulsion is formed in the absence of the addition of emulsifier.

15. The method of claim 8 wherein said step of forming said pseudoemulsion comprises mixing said triglycerides, water and lipase in an impeller blade mixer, wherein said steps of continuously stirring and continuously impelling are carried out in said mixer.

16. The method of claim 15 wherein said triglycerides include minute quantities of polyethylene as an impurity, further comprising forming a thin film of said polyethylene on said mixer's blades during said pseudoemulsion forming and maintaining steps, wherein said film is easily removed from said blades with hot water; and further comprising separating said pseudoemulsion into oil and aqueous layers after said pseudoemulsion contains less than 0.3% of said triglycerides, wherein said layers have a thin film therebetween, wherein said thin film comprises spent lipase and polyethylene, wherein said oil and aqueous layers are polyethylene-free.

17. The method of claim 15 wherein said pseudoemulsion is formed in the absence of the addition of emulsifier.

18. The method of claim 15 wherein the ratio of feedstock volume to total impeller blade area in said mixer, in ml per sq. cm., is no more than about 35:1.

19. The method of claim 18 wherein said pseudomulsion is formed in the absence of the addition of emulsifier.

20. The method of claim 18 wherein said baffles comprise at least 4 radially-positioned baffles in said mixer.

21. The method of claim 20 wherein the speed of mixing is about 200–1500 rpm.

22. The method of claim 21 wherein the speed of mixing is about 400–1000 rpm.

23. The method of claim 15 wherein the ratio of feedstock volume to total impeller blade area in said mixer, in ml per sq. cm., is no more than about 25:1.

24. The method of claim 23 wherein said baffles comprise at least 4 radially-positioned baffles in said mixer.

25. The method of claim 24 wherein the speed of mixing is about 200–1500 rpm.

26. The method of claim 25 wherein the speed of mixing is about 400–1000 rpm.

27. The method of claim 26 wherein the hydrolysis is carried out in a plurality of mixers in a continuous, cascade manner, wherein hydrolysis product in one mixer, prior to completion of hydrolysis therein, is transferred from said one mixer to a mixer immediately downstream, while feed is simultaneously replenished in said one mixer from a mixer immediately upstream.

28. The method of claim 26 wherein there are 4–6 blades on each impeller in said mixer.

29. The method of claim 22 wherein there are 4–6 blades on each impeller in said mixer.

30. The method of claim 29 wherein said triglycerides are in tallow, wherein said lipase is *C. rugosa* lipase, and wherein said mixing is carried out at about 40° C., and below said tallow's melting point.

* * * * *